(12) United States Patent
Kovesdi et al.

(10) Patent No.: US 6,225,289 B1
(45) Date of Patent: May 1, 2001

(54) METHODS AND COMPOSITIONS FOR PRESERVING ADENOVIRAL VECTORS

(75) Inventors: Imre Kovesdi, Rockville; Stephen C. Ransom, Germantown, both of MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/208,666

(22) Filed: Dec. 10, 1998

(51) Int. Cl.$^7$ .......................... A61K 31/70; A61K 47/00; A61K 48/00

(52) U.S. Cl. .......................... 514/23; 514/777; 424/93.2

(58) Field of Search ...................... 514/777, 23; 424/93.2

(56) References Cited

U.S. PATENT DOCUMENTS

| | | | |
|---|---|---|---|
| 3,674,864 | * 7/1972 | Angelucci | 424/90 |
| 3,915,794 | 10/1975 | Zygraich et al. | 195/1.8 |
| 4,337,242 | 6/1982 | Markus et al. | 424/89 |
| 4,338,335 | 7/1982 | McAleer et al. | 424/361 |
| 4,678,812 | 7/1987 | Bollin, Jr. et al. | 514/777 |
| 4,762,857 | 8/1988 | Bollin, Jr. et al. | 514/777 |
| 4,891,319 | 1/1990 | Roser | 435/188 |
| 5,149,653 | * 9/1992 | Roser | 435/260 |
| 5,364,756 | 11/1994 | Livesey et al. | 435/2 |
| 5,792,643 | 8/1998 | Herrmann et al. | 435/235.1 |
| 5,800,978 | 9/1998 | Goodrich, Jr. et al. | 435/2 |
| 5,814,321 | * 9/1998 | Miyahura et al. | 424/278.1 |

FOREIGN PATENT DOCUMENTS

| | | | |
|---|---|---|---|
| 299213 | 4/1992 | (DE) | . |
| 0 415 567 | 3/1991 | (EP) | A61K/47/02 |
| 0 523 406 | 1/1993 | (EP) | . |
| 0 872 249 | 10/1998 | (EP) | A61K/48/00 |
| WO 89/06542 | 7/1989 | (WO) | A61K/39/12 |
| WO 89/06976 | 8/1989 | (WO) | A61K/97/00 |
| WO 91/18091 | 11/1991 | (WO) | C12N/9/96 |
| WO 95/34671 | 12/1995 | (WO) | C12N/15/86 |
| WO 98/56414 | 12/1998 | (WO) | . |

OTHER PUBLICATIONS

Liu et al 126CA:308806, 1998.*
Chu 124CA:66573, 1996.*
Berkner et al., *J. Virol.*, 61, 1213–1220 (1987).
Croyle et al., *Pharmaceutical Development and Technology*, 3 (3), 373–383 (1998).
Curiel et al., *Hum. Gene Ther.*, 3, 147–154 (1992).
Davidson et al., *J. Virol.*, 61, 1226–1239 (1987).
Mansour et al., *Mol. Cell Biol.*, 6, 2684–2694 (1986).
Newman et al., *Biotechnology and Genetic Engineering Reviews*, 11, 263–294 (1993).
Gupta et al., *Vaccine*, 14 (15), 1417–1420 (1996).
Paiva et al., *Biotechnology Annual Review*, 2, 293–314 (1996).

* cited by examiner

*Primary Examiner*—Russell Travers
(74) *Attorney, Agent, or Firm*—Leydig, Voit & Mayer, Ltd.

(57) ABSTRACT

The present invention provides a method and composition for preserving an adenoviral vector. Both the method and composition involve the use of an adenoviral gene transfer vector, a pharmaceutically acceptable liquid carrier, and a stabilizing agent, which enables the adenoviral vector to be maintained at a temperature above 0° C. for at least 7 days.

20 Claims, No Drawings

METHODS AND COMPOSITIONS FOR PRESERVING ADENOVIRAL VECTORS

TECHNICAL FIELD OF THE INVENTION

The present invention relates to methods and compositions useful in preserving adenoviral vectors, particularly adenoviral gene transfer vectors.

BACKGROUND OF THE INVENTION

Modified viruses have proven convenient vector systems for investigative and therapeutic gene transfer applications. Adenoviral vector systems present several advantages for such uses because they are generally associated with benign pathologies in humans, and the 36 kb of the adenoviral genome has been extensively studied. Adenoviral vectors can be produced in high titers (e.g., about $10^{13}$ particle/ml), and such vectors can transfer genetic material to non-replicating, as well as replicating, cells (in contrast with, for example, retroviral vectors which only transfer genetic material to replicating cells). The adenoviral genome can be manipulated to carry a large amount of exogenous DNA (up to about 8 kb), and the adenoviral capsid can potentiate the transfer of even longer sequences (Curiel et al., *Hum. Gene Ther.*, 3, 147–154 (1992)). Additionally, adenoviruses generally do not integrate into the host cell chromosome, but rather are maintained as a linear episome, thus minimizing the likelihood that a recombinant adenovirus will interfere with normal cell function. Aside from being a superior vehicle for transferring genetic material to a wide variety of cell types, adenoviral vectors represent a safe choice for gene transfer, a particular concern for therapeutic applications.

A variety of recombinant adenoviral vectors have been described. Most of the vectors in use today derive from either the adenovirus serotype 2 (Ad2) or serotype 5 (Ad5), members of subgroup C. An exogenous gene of interest typically is inserted into the early region 1 (E1) of the adenovirus. Disruption of the E1 region decreases the amount of viral proteins produced by both the early regions (DNA binding protein) and late regions (penton, hexon, and fiber proteins), preventing viral propagation. These replication deficient adenoviral vectors require growth in either a complementary cell line or in the presence of an intact helper virus, which provides, in trans, the essential E1 functions (Berker et al., *J. Virol.*, 61, 1213–1220 (1987); Davidson et al., *J. Virol.*, 61, 1226–1239 (1987); Mansour et al., *Mol. Cell Biol.*, 6, 2684–2694 (1986)). More recently, adenoviral vectors deficient in both E1 and the early region 4 (E4) have been used to substantially abolish expression of viral proteins. In order to insert the larger genes (up to 8 kb) into the adenoviral genome, adenoviral vectors additionally deficient in the nonessential early region 3 (E3) are used. Multiply deficient adenoviral vectors are described in published PCT patent application WO 95/34671.

The use of adenoviral vectors in investigative and therapeutic applications necessitates that the vectors be transported and stored for a period of time. During this period of storage, the adenoviral vectors desirably are maintained without significant loss of infectivity and/or viability. Adenoviral vectors can be stored frozen at very low temperatures, e.g., −80° C., without significant loss of activity; however, the need for low temperature freezers, which are not widely available, limits the practicality of this approach. Lyophilization, or freeze-drying, is another option for storage of adenoviral vectors. This method has disadvantages as it is expensive, and, upon reconstitution, the adenoviral vector composition is often left for extended periods of time at room temperature (i.e., 20–25° C.). Adenoviral vectors rapidly lose viability when stored at room temperature. Similar problems arise when adenoviral vectors are dried at room temperature.

In view of the above, there exists a need for further methods of, and compositions useful in, the storage or preservation of adenoviral vectors. In particular, there is a need for methods and compositions for storage of adenoviral vectors in a liquid state, rather than a dried or frozen state. The present invention provides such methods and compositions. These and other advantages of the present invention, as well as additional inventive features, will be apparent from the description of the invention provided herein.

BRIEF SUMMARY OF THE INVENTION

The present invention provides a method for stabilizing a viral gene transfer vector comprising (a) preparing a pharmaceutical composition comprising an adenoviral vector, a stabilizing agent and a pharmaceutically acceptable liquid carrier, and (b) maintaining the composition in liquid form at a temperature above 0° C. for at least 7 days. The present invention also provides a pharmaceutical composition comprising an adenoviral gene transfer vector, a pharmaceutically acceptable liquid carrier, and a stabilizing agent selected from the group consisting of polysorbate 80, L-arginine, polyvinylpyrrolidone, trehalose, and combinations thereof, wherein the composition can be maintained in liquid form at a temperature above 0° C. for at least 7 days such that the activity of said composition decreases 20% or less after 7 days.

DETAILED DESCRIPTION OF THE INVENTION

The present invention provides a method for satisfactorily preserving (i.e., storing) an adenoviral gene transfer vector in a pharmaceutical composition at a temperature above 0° C. for at least 7 days. This invention further provides the pharmaceutical composition for such a purpose, which pharmaceutical composition comprises an adenoviral gene transfer vector, a pharmaceutically acceptable liquid carrier, and a stabilizing agent. The present inventive method and composition desirably preserves an adenoviral gene transfer vector with an acceptable decrease in activity during storage at relatively high temperatures for extended periods of time.

The term "activity," as used in describing the present invention, is a measure of the viability of a composition of an adenoviral gene transfer vector. Activity is a measure of the amount of gene product produced by cells (e.g., 293 cells or preferably A549 cells) infected by a sample comprising the adenoviral vector containing the gene (i.e., the adenoviral gene transfer vector).

The adenoviral gene transfer vector composition is maintained at a temperature such that the composition remains in liquid form (i.e., temperatures above freezing, thereby preventing viral inactivation). Typically, the adenoviral gene transfer vector composition is maintained at a temperature above 0° C., preferably at 4° C. or higher (e.g., 4–10° C.). In some embodiments, it is desirable to maintain the adenoviral gene transfer vector composition at a temperature of 10° C. or higher (e.g., 10–20° C.), 20° C. or higher (e.g., 20–25° C.), or even 30° C. or higher (e.g., 30–40° C.), such as may be encountered under non-environmentally controlled ambient conditions (which can result in the adenoviral gene transfer vector composition being exposed to a variety of non-freezing temperatures of, for example, 4–37° C.).

The adenoviral gene transfer vector composition is maintained for various periods of time. The adenoviral gene transfer vector desirably is maintained at the aforementioned temperature(s) for at least 1 day (e.g., 7 days (1 week) or more), though typically the time period will be longer, such as at least 3, 4, 5, or 6 weeks, or even longer, such as at least 10, 11 or 12 weeks. During that time period, the adenoviral gene transfer vector optimally loses no, or substantially no, activity, although some loss of activity is acceptable, especially with relatively higher storage temperatures and/or relatively longer storage times.

The present inventive method and composition desirably preserve an adenoviral gene transfer vector at a temperature above 0° C., preferably at a temperature of 4° C., such that the activity of the adenoviral gene transfer vector composition decreases about 20% or less, preferably about 10% or less, and more preferably about 5% or less, after any of the aforementioned time periods, especially after 7 days. Most preferably, the present inventive method and composition preserve an adenoviral gene transfer vector at a temperature above 0° C., preferably at a temperature of 4° C., such that the activity of the adenoviral gene transfer vector composition remains substantially or actually the same after any of the aforementioned time periods, especially after 7 days.

The present inventive method and composition also desirably preserve an adenoviral gene transfer vector at a temperature above 20° C., preferably at a temperature of 37° C., such that the activity of the adenoviral gene transfer vector composition decreases about 50% or less, preferably about 40% or less, and more preferably about 30% or less, after any of the aforementioned time periods, especially after 10 weeks. Most preferably, the present inventive method and composition preserve an adenoviral gene transfer vector at a temperature above 20° C., preferably at a temperature of 37° C., such that the activity of the adenoviral gene transfer vector composition remains substantially or actually the same after any of the aforementioned time periods, especially after 10 weeks.

The stabilizing agent is selected from the group consisting of polysorbate 80, L-arginine, polyvinylpyrrolidone, α-D-glucopyranosyl α-D-glucopyranoside dihydrate (commonly known as trehalose), and combinations thereof. More preferably, the stabilizing agent is trehalose, or trehalose in combination with polysorbate 80.

The stabilizing agent can be present in any suitable concentration in the adenoviral gene transfer vector composition. When the stabilizing agent is trehalose, the trehalose desirably is present in a concentration from about 2–10% (wt./vol.), preferably about 4–6% (wt./vol.) of the adenoviral gene transfer vector composition. When trehalose and polysorbate 80 are present in the adenoviral gene transfer vector composition, the trehalose preferably is present in a concentration of about 4–6% (wt./vol.), more preferably about 5% (wt./vol.), while the polysorbate 80 desirably is present in a concentration of about 0.001–0.01% (wt./vol.), more preferably about 0.0025% (wt./vol.).

The pharmaceutically acceptable liquid carrier can be any suitable such carrier. Preferably, the pharmaceutically acceptable liquid carrier contains a buffer and a salt. In some embodiments, particularly when the stabilizing agent is polysorbate 80, L-arginine, or polyvinylpyrrolidone, the pharmaceutically acceptable liquid carrier preferably contains a saccharide other than trehalose.

The present invention is further described in the following examples. These examples serve only to illustrate the invention and are not intended to limit the scope of the invention in any way.

EXAMPLES

Example 1

This example compares the effect of various saccharides on the preservation of an adenoviral vector composition.

A series of pharmaceutical compositions were prepared. Each pharmaceutical composition contained an adenoviral gene transfer vector, water, 10 mM Tris (pH 7.8 at room temperature (i.e., 20–25° C.)), 75 mM NaCl, and 2% (wt./vol.), 3% (wt./vol.), 5% (wt./vol.), or 10% (wt./vol.) of one of the following saccharides: sorbital, trehalose, sucrose, mannitol, or dextrose. The adenoviral gene transfer vector was E1 and E3 deficient with a reporter gene, secretory alkaline phosphatase (SEAP), under control of the cytomegalovirus (CMV) promoter, inserted in the E1 region. Each pharmaceutical composition was stored at 37° C. for 7 days, and then the activity of the composition was determined. Activity is a measure of the SEAP produced upon infection of A549 cells with a sample of the adenoviral gene transfer vector composition. The present decrease in activity for each pharmaceutical composition is set forth in Table 1.

TABLE 1

| Saccharide | Percent Decrease in Activity of Adenoviral Vectors Stored for 7 Days at 37° C. | | | |
| --- | --- | --- | --- | --- |
|  | 2%* Solution | 3%* Solution | 5%* Solution | 10%* Solution |
| Sorbital | 100 | 100 | 99 | 99 |
| Trehalose | 57 | 42 | 28 | 25 |
| Sucrose | 100 | 100 | 100 | 99 |
| Mannitol | 100 | 100 | 100 | 99 |
| Dextrose | 100 | 100 | 100 | 100 |

*% refers to (wt./vol.)

As is apparent from the experimental results set forth in Table 1, trehalose was the most effective stabilizing agent for the adenoviral vector stored for seven days at 37° C. The other saccharides—sorbital, sucrose, mannitol and dextrose—exhibited little or no stabilizing effect on the adenoviral vectors. These results demonstrate that trehalose stabilizes adenoviral vector compositions sufficiently such that the adenoviral vectors can be stored for 7 days at non-environmentally controlled ambient conditions, e.g., at temperatures of up to 37° C.

Example 2

This example illustrates the ability of a 5% (wt./vol.) solution of trehalose to stabilize an adenoviral vector composition.

Pharmaceutical compositions were prepared in accordance with Example 1, except that only trehalose was used as the stabilizing agent at a concentration of 5% (wt./vol.). The pharmaceutical compositions were stored at various temperatures—4° C., 25° C., or 37° C.—for various periods of time—1 day, 1 week, 3 weeks, 6 weeks, and 11 weeks. The activity of the pharmaceutical composition was determined in the same manner as Example 1 for each pharmaceutical composition after the indicated storage period, and the percent decrease in activity for each pharmaceutical composition is set forth in Table 2.

TABLE 2

| Time | Percent Decrease in Activity of Adenoviral Vectors Stored with 5% (wt./vol.) Trehalose | | |
| --- | --- | --- | --- |
| | 4° C. | 25° C. | 37° C. |
| 1 day | 2 | 7 | 0 |
| 1 week | 2 | 23 | 66 |
| 3 weeks | 2 | 28 | 90 |
| 6 weeks | 0 | 53 | 100 |
| 11 weeks | 10 | 79 | 100 |

As is apparent from the experimental results set forth in Table 2, 5% (wt./vol.) trehalose was most effective in stabilizing the adenoviral vector under 4° C. storage conditions. The activity of the adenoviral vector composition after 11 weeks had decreased only about 10%. At room temperature (i.e., 20–25° C.), the activity of the adenoviral vector composition had decreased about 25% after 1 week, and about 79% after 11 weeks. For the adenoviral vector compositions stored at 37° C., the activity decreased about 70% after 1 week. These results demonstrate that 5% (wt./vol.) trehalose stabilizes an adenoviral vector at a range of temperatures and for extended periods of time.

Example 3

This example illustrates the ability of trehalose and polysorbate 80 to act as a stabilizing agent for adenoviral vectors.

Pharmaceutical compositions were prepared in accordance with Example 1, except that 5% (wt./vol.) trehalose and 0.0025% (wt./vol.) polysorbate 80 were used as the stabilizing agent. The pharmaceutical compositions were stored and evaluated in the same manner set forth in Example 2. The activity of the pharmaceutical composition was determined for each pharmaceutical composition after the indicated storage period, and the percent decrease in activity for each pharmaceutical composition is set forth in Table 3.

TABLE 3

| Time | Percent Decrease in Activity of Adenoviral Vectors Stored with Trehalose and Polysorbate 80 | | |
| --- | --- | --- | --- |
| | 4° C. | 25° C. | 37° C. |
| 1 day | 0 | 5 | 14 |
| 1 week | 0 | 6 | 41 |
| 3 weeks | 5 | 25 | 84 |
| 6 weeks | 0 | 44 | 100 |
| 11 weeks | 5 | 77 | 100 |

As is apparent from the experimental results set forth in Table 3, trehalose and polysorbate 80 were most effective in stabilizing the adenoviral vector under 40° C. storage conditions. After 1 week, the activity of the adenoviral vector composition had not significantly diminished, and after 11 weeks, the activity had only decreased about 5%. At room temperature (i.e., 20–25° C.), the activity of the adenoviral vector composition had decreased about 50% after 6 weeks, and about 80% after 11 weeks. For the adenoviral vector compositions stored at 37° C., the activity decreased about 40% after 1 week, and about 85% after 3 weeks. These results demonstrate that trehalose and polysorbate 80 are effective at stabilizing an adenoviral vector at a range of temperatures for extended periods of time.

Example 4

This example illustrates the ability of various excipients to stabilize adenoviral vector compositions.

Three pharmaceutical compositions were prepared in a manner similar to that set out in Example 1. Each pharmaceutical composition contained an adenoviral gene transfer vector, water, 10 mM Tris (pH 7.8 at room temperature, i.e. 20–25° C.), 75 mM NaCl, 3% (wt./vol.) sucrose, and either 0.0025% (wt./vol.) polysorbate 80, 20 mM L-arginine, or 0.1% (wt./vol.) polyvinylpyrrolidone. Each pharmaceutical composition was stored at 37° C. for 4 days, and then the activity of the composition was determined. The percent decrease in activity for each pharmaceutical composition is set forth in Table 4.

TABLE 4

| Stabilizer | Percent Decrease in Activity of Adenoviral Vectors Stored for 4 Days at 37° C. |
| --- | --- |
| Polysorbate 80 | 31 |
| L-arginine | 42 |
| Polyvinylpyrrolidone | 53 |

As is apparent from the experimental results set forth in Table 4, polysorbate 80 alone had a moderate stabilizing effect on the activity of adenoviral vectors (about 30% activity decrease), while the other excipients, L-arginine and polyvinylpyrrolidone, exhibited less of a stabilizing effect on the adenoviral vector (about 40% and 50% activity decreases, respectively). These results demonstrate that polysorbate 80 L-arginine, and polyvinylpyrrolidone can be useful, alone or preferably in combination with other stabilizing agents, in preserving adenoviral vectors.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for preserving an adenoviral gene transfer vector in a liquid carrier, which method comprises:
   (a) preparing a pharmaceutical composition comprising an adenoviral gene transfer vector, a pharmaceutically acceptable liquid carrier, and a stabilizing agent selected from the group consisting of polysorbate 80, L-arginine, polyvinylpyrrolidone, trehalose, and combinations thereof, and
   (b) maintaining said composition as a liquid at a temperature above 0° C. for at least 7 days with a decrease in activity of said composition of about 20% or less.

2. The method of claim 1, wherein said stabilizing agent is trehalose.

3. The method of claim 2, wherein said trehalose is present in said composition in a concentration of about 2–10% (wt./vol.).

4. The method of claim 2, wherein said stabilizing agent is a mixture of trehalose and polysorbate 80.

5. The method of claim 1, wherein said pharmaceutically acceptable carrier comprises a buffer and a salt.

6. The method of claim 5, wherein said pharmaceutically acceptable carrier further comprises a saccharide other than trehalose.

7. The method of claim 2, wherein the activity of said composition decreases about 20% or less after 7 days.

8. The method of claim 7, wherein the activity of said composition remains substantially the same after 7 days.

9. The method of claim 2, wherein said composition is maintained at a temperature above 0° C. for at least 10 weeks.

10. The method of claim 9, wherein the activity of said composition decreases about 50% or less after 10 weeks.

11. The method of claim 2, wherein said composition is maintained at a temperature of 37° C. or higher for at least 7 days.

12. The method of claim 11, wherein the activity of said composition decreases about 50% or less after 7 days.

13. A liquid pharmaceutical composition comprising an adenoviral gene transfer vector, a pharmaceutically acceptable liquid carrier, and a stabilizing agent selected from the group consisting of polysorbate 80, L-arginine, polyvinylpyrrolidone, trehalose, and combinations thereof, wherein said composition can be maintained as a liquid at a temperature above 0° C. for 7 days with a decrease in activity of said composition of about 20% or less.

14. The composition of claim 13, wherein said stabilizing agent is trehalose.

15. The composition of claim 14, wherein said trehalose is present in said composition in a concentration of about 2–10% (wt./vol.).

16. The composition of claim 15, wherein said trehalose is present in a concentration of about 4–6% (wt./vol.).

17. The composition of claim 13, wherein said stabilizing agent is a mixture of trehalose and polysorbate 80.

18. The composition of claim 17, wherein said trehalose is present in said composition in a concentration of about 4–6% (wt./vol.) and said polysorbate 80 is present in said composition in a concentration of about 0.001–0.01% (wt./vol.).

19. The composition of claim 13, wherein said pharmaceutically acceptable carrier comprises a buffer and a salt.

20. The composition of claim 19, wherein said pharmaceutically acceptable carrier further comprises a saccharide other than trehalose.

* * * * *